United States Patent [19]
Stöferle et al.

[11] 4,103,538
[45] Aug. 1, 1978

[54] SURFACE HARDNESS TESTING APPARATUS

[76] Inventors: Theodor Stöferle, Weinbergstr. 29, D-6101 Seeheim; Paul Heinz Theimert, Gerhart-Hauptmann 10, D-6101 Weiterstadt, both of Germany

[21] Appl. No.: 788,661

[22] Filed: Apr. 18, 1977

[30] Foreign Application Priority Data

Apr. 20, 1976 [DE] Fed. Rep. of Germany ....... 2617256

[51] Int. Cl.² ............................................. G01N 3/46
[52] U.S. Cl. ..................................................... 73/81
[58] Field of Search ............................... 73/81, 85, 105

[56] References Cited
U.S. PATENT DOCUMENTS 2,620,655  12/1952  Priest ..................... 73/105

FOREIGN PATENT DOCUMENTS 506,586  1/1926  Fed. Rep. of Germany .............. 73/81

*Primary Examiner*—Jerry W. Myracle
*Attorney, Agent, or Firm*—David A. Burge Co.

[57] ABSTRACT

An apparatus for measuring the hardness of a succession of adjacent portions of a test surface, utilizes a pair of members which are supported for independent movement in close, side-by-side relationship in engagement with a test surface. One of the members is a "penetration member" which is selectively loaded with a controlled weight for penetrating the test surface. The other of the members is a "sensor member" which is held relatively gently against the test surface. A motion sensing transducer is interposed between the two members to sense the depth of penetration of the penetration member into the test surface. The members are pivotally mounted on an adjustable positioning mechanism in such a manner that the controlled loading applied to the penetration member is not transmitted to and does not distort sensor data provided by the sensor member. Loading is transmitted to the penetration member through a hardened steel ball to eliminate transverse force components and bending moments. Other features are described which enhance the accuracy of operation of the sensing apparatus.

15 Claims, 13 Drawing Figures

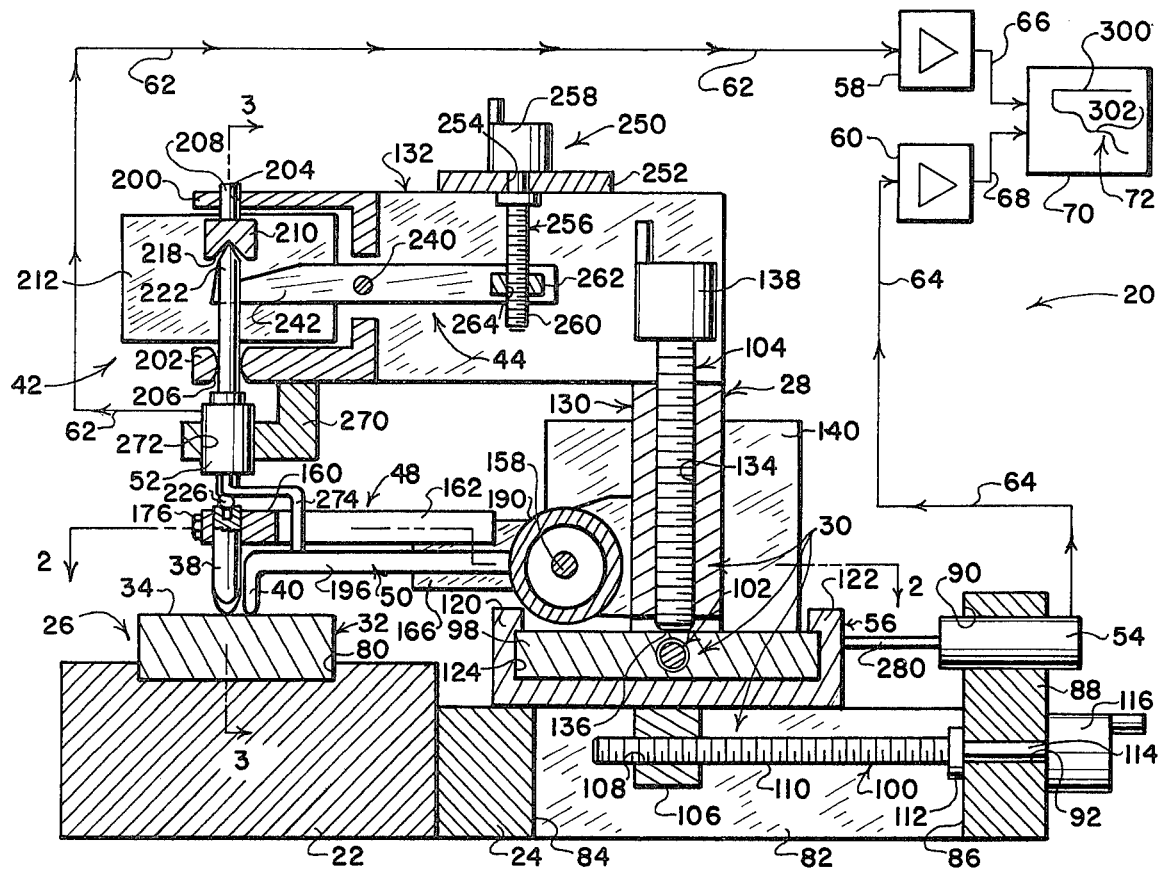
FIG. 1
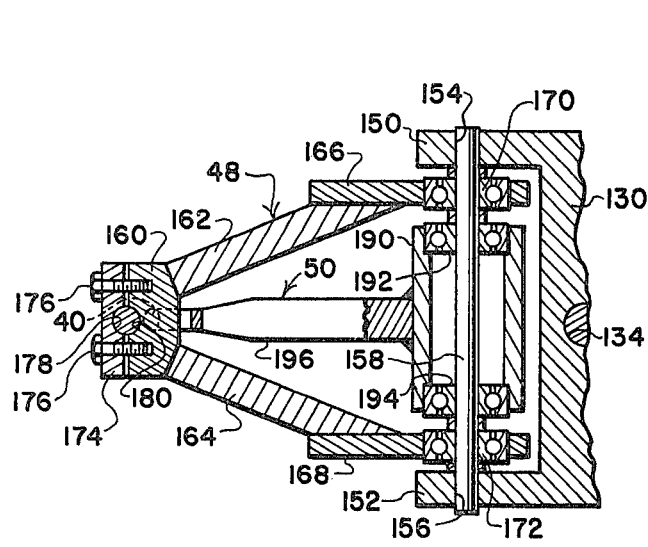
FIG. 2
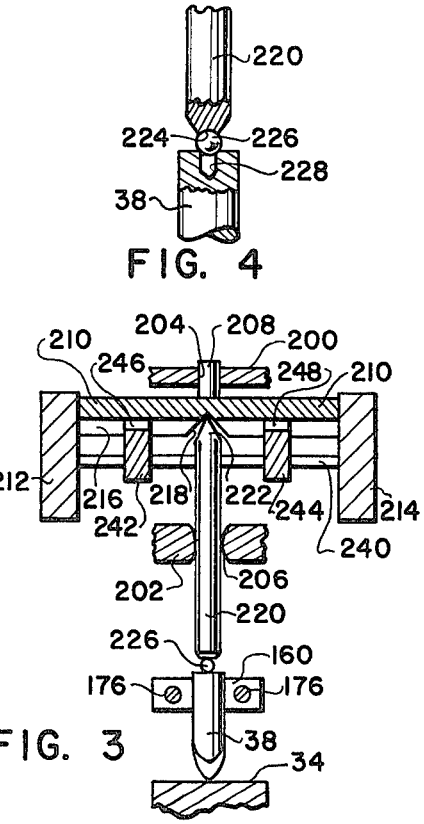
FIG. 4
FIG. 3

SURFACE HARDNESS TESTING APPARATUS

BACKGROUND OF THE INVENTION

1. Field of the Invention

The present invention relates generally to apparatus for testing surface hardness of a specimen, and, more paticularly, to a novel and improved hardness testing apparatus adapted to accurately sense variations in surface hardness among a succession of adjacent test surface portions.

2. Prior Art

Hardness testing apparatus of the "continuous" type adapted to measure variations in surface hardness among a succession of adjacent test surface portions is known. One known device of this type utilizes a pair of members which are pivoted side-by-side and close to each other on a slide, and which can move in an end plate. The members both engage a test surface and are configured such that relative movement can be effected between the test surface and the members in directions paralleling the plane of the test surface so that the members are brought into engagement with a succession of adjacent test surface portions. One of the members is known as a "penetration member" and is loaded in a controlled manner, causing it to penetrate the test surface. The other of the members is a "sensor member" and it is simply held in firm, non-penetrative engagement with the test surface. A relative motion sensing transducer is interposed between the two members to sense their relative movement, whereby the transducer's output signal is representative of the depth to which the penetration member has penetrated the test surface at a given time.

As is understood by those skilled in the art, the depth to which the penetration member has penetrated the test surface, in response to a particular loading of the penetration member, is a function of surface hardness. Surface hardness can be ascertained from knowledge of the penetration depth, knowledge of the loading of the penetration member, and knowledge of construction of such portions of the penetration member as are caused to penetrate the test surface.

The proposed device utilizes a first transducer to sense relative movement between the penetration and sensor members, and a second transducer to sense relative movement between the slide and the base of the device. By this arrangement, an orthogonal or "X-Y" plot can be made with sensed hardness represented by units of distance along one axis and with position along the test surface represented by units of distance along an orthogonally extending axis.

A problem with the proposed device is that the sliding motion which takes place with its construction and arrangement of components results in the relatively large force required to move the penetration member being applied along the test surface, and deformations caused by this force are found to act, at least partially, on the sensor member. When these forces act on the sensor member, distortions may be introduced into the test results, particularly with regard to the measurement of travel sensed by the transducer attached to the slide.

SUMMARY OF THE INVENTION

The present invention overcomes the foregoing and other drawbacks of the prior art by providing a novel and improved continuous hardness testing apparatus.

Hardness testing apparatus constructed in accordance with the preferred practice of the present invention are less susceptible to measurement error, particularly error caused by forces acting on the penetration member. The present invention provides a sensor member mounting arrangement which permits the operation of the sensor member to remain isolated from and uninfluenced by the operation of such elements as transmit forces to the penetration member. The components which guide and retain the sensor member are substantially removed from the flux of the force transmitted to the penetration member, thereby permitting accurate measurements to be taken with elements which are gently loaded.

In one embodiment of the invention, an arm bearing the penetration member and an arm bearing the sensor member are mounted on a common shaft with the bearings of the two arms and/or the bearings of the shaft being arranged symmetrically with respect to a common plane. In this manner, the bearings of the penetration member arm and of the sensor member arm can be disposed very near each other in an inexpensive, compact construction, and forces and deformations caused by the forces acting on the penetration member do not influence the operation of the sensor member.

Even better separation can be attained, with a slight increase in bulk, by pivotally mounting the penetration member arm and the sensor member arm about two closely spaced but separate shafts. Accuracy of operation is not reduced if the axes of rotation of the sensor member arm and of the penetration member arm do not exactly coincide.

Still another feature of the present invention which helps to reduce interaction between the sensor member and the penetration member lies in mounting the sensor member on a bearing so that it can move at right angles to the test surface, and by mounting the penetration member on an arm which can pivot around a bearing point. Since the sensor member is not subject to any appreciable force, it can be disposed in a very simple vertical guide. Since the penetration member is subjected to relatively high pressure and lateral tensile forces, it is preferably pivotally connected to a machine slide which is designed to provide accurate guidance with relatively low friction, even when subjected to relatively high forces.

Still another feature designed to increase the accuracy of measurement is the utilization of a ball or conical bearing guide to transmit a controlled test force to the penetration member. The ball is positioned above the center of gravity of the penetration member and operates to transmit substantially only vertical force components without any transverse components and/or bending loads on the penetration member. Due to the independent action of the penetration member and the sensor member, the sensor member remains completely unaffected by forces acting on the penetration member.

Still another feature of the invention lies in the provision of a system for relieving the weight force applied to the penetration member at times when a hardness test is not being conducted. By this arrangement, the weight force can be freely lifted off the ball or conical bearing so that the penetration member can be gently loaded and unloaded.

In one embodiment of the present invention, a motion sensing transducer is provided for determining the motion of the penetration member relative to the sensor member in directions paralleling the test surface, and the motion sensing transducer is connected directly to the penetration member. This arrangement assures that the motion sensing transducer directly measures the distance travelled by the penetration member without being influenced by any play or clearances in bearings or guides.

In one embodiment of the invention, the sensor member is offset relative to the penetration member at an angle relative to the direction of motion executed by the members over the test surface. This feature is particularly advantageous if a preliminary test force is used, in which case, the furrow produced by the penetration member may otherwise interfere with the operation of the sensor member.

In accordance with another feature of the invention, the penetration member is mounted in such a way as facilitates its rapid replacement. In addition, the penetration member has at least one guide surface for aligning it along a matching surface formed in a clamping and mounting member. Since the penetration member must always be moved over the test surface in a particular direction depending on its shape, the last mentioned feature insures that the penetration member is always mounted in the right position after being replaced. These features combine to facilitate rapid and accurate replacement of a penetration member.

In accordance with still another feature of the invention, the penetration member has a penetration point defined by portions of two conical surfaces, the axes of the two cones of which extend on opposite sides of the penetration member at a distance from and paralleling the longitudinal axis of the penetration member. A penetration member point having this shape can be manufactured more easily and more accurately than if the shape is substantially the same in the penetration point region but having two axes of the boundary cones coinciding. The result of this advantageous configuration of the penetration point is to increase accuracy and to improve the reliability of the test results.

As will be apparent from the foregoing summary, it is a general object of the present invention to provide a novel and improved hardness testing apparatus which will measure surface hardness with minimal error.

Other objects and a fuller understanding of the invention may be had by referring to the following description and claims taken in conjunction with the accompanying drawings.

BRIEF DESCRIPTION OF THE DRAWINGS

FIG. 1 is a schematic view substantially in cross-section, of a hardness tester incorporating one embodiment of the present invention;

FIG. 2 is a sectional view as seen from planes indicated by a broken line 2—2 in FIG. 1;

FIG. 3 is a sectional view as seen from a plane indicated by a line 3—3 in FIG. 1;

FIG. 4 is an enlargement of a portion of the structure shown in FIG. 3, with portions broken away and shown in cross-section;

DESCRIPTION OF THE PREFERRED EMBODIMENTS

Figure 5:
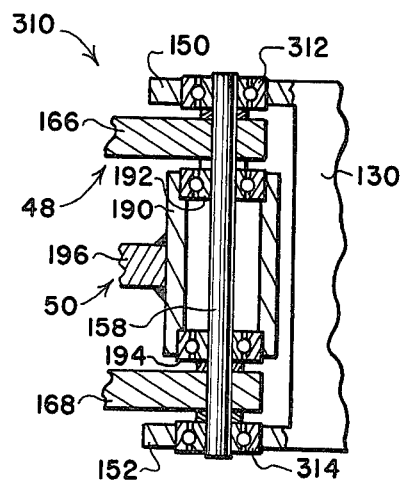
FIG. 5 is a view similar to FIG. 2 of an alternate embodiment of the present invention.

Referring to FIG. 1, a continuous hardness tester apparatus is indicated generally by the numeral 20. The apparatus 20 includes a base assembly of connected forward and rearward members 22, 24. The forward base member 22 defines a test station indicated generally by the numeral 26. The apparatus 20 additionally includes an upstanding structure 28 supported for movement relative to the base assembly 22 by a three-coordinate drive system 30.

As will be explained in greater detail, a specimen 32 having a surface 34 to be tested for hardness is supported in the test station 26 with its test surface 34 facing upwardly. A pair of members 38, 40 engage the test surface 34. The member 38 is known as a "penetration member" and is selectively forced into penetrative engagement with the test surface 34 by a weight arrangement 42. A weight-force relieving mechanism 44 is provided to restrain the weight arrangement 42 to relieve forces applied to the penetration member 38 when a hardness test is not in progress. The member 40 is a "sensor member" and it rests gently on the test surface 34. The members 38, 40 are supported by pivotally movable arms 48, 50 for entirely independent relative movement. A first transducer 52 is interposed between the members 38, 40 to sense their relative vertical movement, and a second transducer 54 is interposed between the base assembly 22 and a forwardly and rearwardly movable carriage 56 to sense their relative movement. The carriage 56 forms part of the drive system 30, as will be explained. Output signals from the transducers 52, 54 are fed through separate amplifiers 58, 60, as indicated by arrows 62, 64, and 66, 68 to the absissa and ordinate input terminals of an orthogonal or "X-Y" recorder apparatus 70. The recorder apparatus 70 is operable to produce a graphical representation 72 of the degree to which the penetration member 38 penetrates the test surface 34 at a succession of adjacent locations across the test surface 34.

Turning now to a more specific description of components of the apparatus 20, the forward base member 22 is provided with a recess 80, within which the test member 32 is positioned and supported. The rearward base member 24 is rigidly connected to the forward base member 22 by any suitable means such as welding, and is provided with an elongate slot 82 bounded at opposite ends by forward and rearward walls 84, 86. The rearward base member 24 has an upstanding part 88, forwardly facing portions of which define the rearward wall 86. Upper and lower holes 90, 92 are formed through the part 88 and open through the wall 86.

The three-coordinate drive system 30 includes the forwardly and rearwardly movable carriage 56, a transversely movable slide 98, and three threaded spindles 100, 102, 104. The carriage 56 is positioned atop a portion of the rearward base member 24 for sliding movement in forward and rearward directions, i.e., leftwardly and rightwardly as viewed in FIG. 1. A drive block 106 is secured to the underside of the carriage 56 and depends into the slot 82. A threaded hole 108 is formed through the drive block 106.

The spindle 100 includes a threaded forward portion 110 which is threaded through the hole 108, an enlarged diameter shoulder portion 112 which abuts the surface 86, and a rearward portion 114 which is journaled in the lower hole 92 and which connects with a crank 116. When the crank 116 is rotated in one direction, the spindle 100 threads through the drive block 106 causing the carriage 56 to move forwardly. When the crank 116 is rotated in the opposite direction, the carriage 56 moves rearwardly.

The carriage 56 has forward and rearward upstanding portions 120, 122 which define a slide channel 124. The slide 98 is supported in the channel for sliding movement relative to the carriage in a horizontal plane extending orthogonally, i.e., transversely, to the path of movement of the carriage 56. The spindle 102 is interposed between the slide 98 and the carriage 56, and is provided with a crank (not shown), in the same manner as the spindle 100 is interposed between the base member 24 and the carriage 56, for effecting relative transverse movements between the slide 98 and the carriage 56.

The upstanding structure 28 includes rigidly interconnected vertical and horizontal mounts 130, 132. A threaded hole 134 is formed through the vertical mount 130. The spindle 104 is threaded through the hole 134. The spindle 104 has a lower end 136 which bears against the slide 98, and an upper end which carries a crank 138. A guide structure 140 is rigidly secured to the slide 98 and engages the vertical mount 130 to support the mount 130 for vertical movement relative to the slide 98. When the crank 138 is rotated in one direction, the mount 130 is caused to thread upwardly along the spindle 104. When the crank 138 is rotated in the opposite direction, the mount 130 is caused to thread downwardly along the spindle 104. As will be apparent, the described drive system 30 provides a simple three-dimensional means for positioning the upstanding structure 28 in forward-rearward, transverse, and vertical directions relative to the assembly of the base members 22, 24.

Referring to FIG. 2, the vertical mount 130 has a pair of forwardly projecting formations 150, 152. Aligned holes 154, 156 are formed through the formations 150, 152, and a shaft 158 has its opposite ends supported in the holes 154, 156. The shaft 158 serves as a support for the arms 48, 50.

The arm 48 includes a welded bifurcate assembly including a head portion 160, a pair of arm portions 162, 164, and a pair of support portions 166, 168. A pair of bearings 170, 172 are carried in holes formed through the support portions 166, 168, and journal the shaft 158. A clamping block 174 is secured by threaded fasteners 176 to the head portion 160. The penetration member 38 is positioned in semicircular recesses 178, 180 formed in the clamping block 174 and in the head portion 160, and is clamped in place by the threaded fasteners 176. By this arrangement, the penetration member 38 is mounted for pivotal movement about the axis of the shaft 158.

The arm 50 includes a cylindrical portion 190 which carries bearings 192, 194 journaled on the shaft 158, and an elongate portion 196 which interconnects the sensor member 40 and the cylindrical portion 190. By this arrangement, the sensor member 40 is mounted for pivotal movement about the axis of the shaft 158.

Referring to FIGS. 1 and 3 the horizontal mount 132 includes upper and lower forward portions 200, 202. Aligned holes 204, 206 are formed through the portions 200, 202. A cylindrical guide rod 208 is slidably carried in the upper hole 204. A weight support bar 210 is rigidly connected to the guide rod 208 and carries a pair of weights 212, 214. A V-shaped downwardly facing groove 216 is formed in the underside of the bar 210, and a conical depression 218 is formed in the underside of the bar 210 concentric with the axis of the rod 208. A plunger 220 extends through the lower hole 206 and has a pointed upper end 222 extending into the conical depression 218.

Referring to FIG. 4, the lower end of the plunger 220 is hollowed out, as indicated by the numeral 224, to receive a hardened steel ball 226. The upper end of the penetration member 38 is provided with a hole 228 which also receives the ball 226. By virtue of this arrangement, and by virtue of the fact that the walls of the lower hole 206 are rounded, as seen in FIGS. 1 and 3, the plunger 220 operates to transmit only vertical force components to the penetration member 38.

Referring to FIGS. 1 and 3, the weight-force relieving mechanism 44 includes a horizontally, transversely extending shaft 240 carried by the horizontal mount 132. A pair of arms 242, 244 are pivotally supported on the shaft 240. The arms 242, 244 have pointed forward ends 246, 248 which extend into the V-shaped groove 216 and engage the weight support bar 210.

A crank and spindle assembly 250 is interposed between the rearward ends of the arms 242, 244 and the horizontal mount 132 to pivot the arms 242, 244 about the axis of the shaft 240. The assembly 250 includes a plate 252 rigidly secured to the mount 132. A hole 254 is formed through the plate 252. A spindle 256 carries a crank 258 on its upper end, depends through the hole 254, and has a threaded lower end 260. A bar 262 interconnects the arms 242, 244. A threaded hole 264 is formed through the bar 262. The lower end 260 of the spindle 256 is threaded through the hole 264. When the crank 258 is rotated in one direction, the bar 262 is moved downwardly, causing the levers 242, 244 to pivot clockwise and causing the weight support bar 210 and the weights 212, 214 to be lifted to relieve weight forces applied to the penetration member 38. When the crank 258 is rotated in the opposite direction, the levers 242, 244 pivot counterclockwise about the axis of the shaft 240 permitting the full weight of the bar 210 and the weights 212, 214 to be applied to the penetration member 38.

An L-shaped extension 270 is provided on the horizontal mount 132. A hole 272 is formed through the extension 270. The transducer 52 is supported in the hole 272 and has a feeler arm 274 which connects with the sensor member arm 196.

The transducer 54 is mounted in the base member hole 90 and has a feeler arm 280 which connects with the carriage 56. The transducers 52, 54 are of a conventional construction and provide a change in electrical output signals in response to sensed relative movements between the members 38, 40 and between the base and carriage members 24, 56, respectively.

A feature of the described arrangement of components is that the forked shape of the penetration member support arm 48 permits lateral forces to be applied without causing any relatively large deformation. Moreover, owing to the symmetrical position of the bearing arrangement shown in FIG. 2, the sensor 40 remains substantially uninfluenced by forces and deformations caused by forces acting on the penetration member 38.

In operation, the three dimensional coordinate drive system 30 of the apparatus 20 is initially adjusted to position the members 30, 40 at the height of the test surface 34. With the members 38, 40 in the position shown in FIG. 1, and with the arms 242, 244 pivoted clockwise to relieve the load of the weights 212, 214 on the penetration member 38, the crank 16 is rotated to effect relative movement between the test member 32 and the members 38, 40. When this is done, a reference line 300 is recorded by the recording apparatus 70. Any error or irregularity in the shape of the test surface is recorded at this time. Next, the weight relieving mechanism 44 is adjusted to impose the full load of the weights 212, 214 on the penetration member 38 whereafter the crank 116 is rotated in the opposite direction to effect opposite relative movement between the test specimen and the members 38, 40. During this process, the penetration member 38 penetrates into the test surface 34 to an extent varying with the hardness of the test surface portions contacted by the penetration member. As a result, the penetration member 38 moves vertically relative to the sensor member 40, and a corresponding line 302 is recorded on the recording apparatus 70. The distance between the reference line 300 and the line 302 represents the depth of penetration of the penetration member into the test surface 34, which depth can be interpreted in a conventional manner to determine the hardness of the test surface portions contacted by the penetration member 38.

As will be apparent to those skilled in the art, the entire described test procedure can be automated by sequential control. Moreover, if the measuring head is adjusted at an angle relative to the direction of measurement, a number of measured lines can be recorded on the apparatus 70, side-by-side and, if the zero-point is correspondingly adjusted, a three-dimensional hardness graph can be recorded by the apparatus 70.

An alternate embodiment of a mounting arrangement for the penetration member arm 48 and for the sensor member arm 50 is indicated generally by the numeral 310 in FIG. 5. In FIG. 5, the bifurcated ends 166, 168 of the penetration member arm 48 are secured directly to the pivot shaft 158 and bearings 312, 314 are used to journal the pivot shaft in the projections 150, 152. All other features of the arrangement are as shown in FIG. 2.

Figure 6:
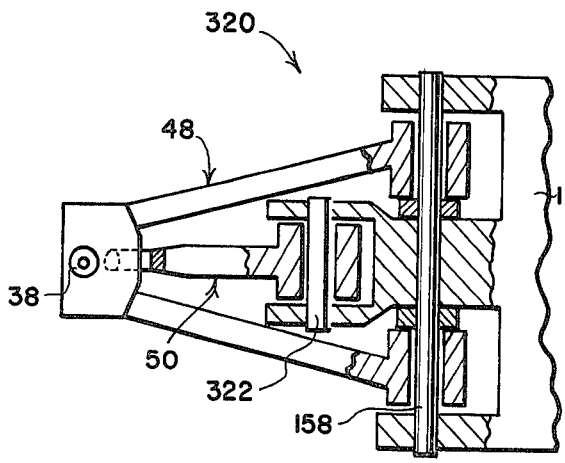
FIG. 6 is a view similar to FIGS. 2 and 5 of still another alternate embodiment.
Figure 7:
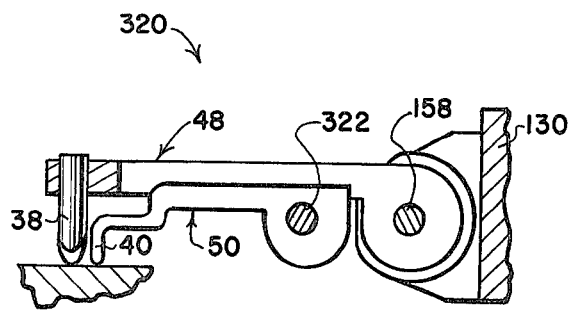
FIG. 7 is a side elevational view of the structure shown in FIG. 6.

Referring to FIGS. 6 and 7, still another possible embodiment of a mounting system for the arms 48, 50 is indicated generally by the numeral 320. In the embodiment 320, the arm 48 is pivotally mounted on the shaft 158, much in the manner of FIG. 2, while the arm 50 is mounted on a separate mounting shaft 322. The shafts 158, 322 are relatively closely spaced and have axes which parallel each other.

Figure 8:
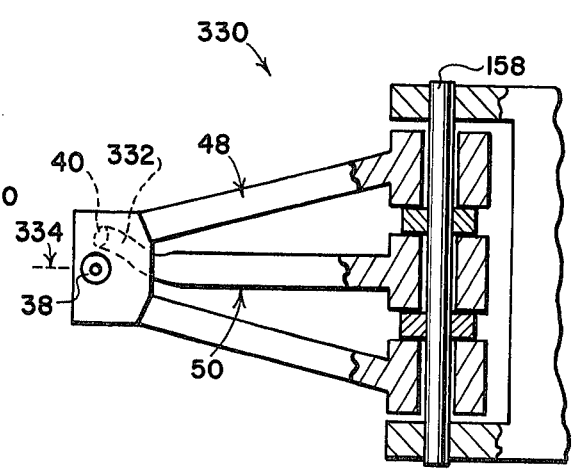
FIG. 8 is a view similar to FIGS. 2, 5 and 6 of still another embodiment.

Referring to FIG. 8, still another possible mounting arrangement of the arms 48, 50 is indicated generally by the numeral 330. In the embodiment 330, the arms 48, 50 are mounted on a common pivot shaft 158 and the sensor arm 50 has a doglegged forward end region 332 which positions the sensor member 40 at a location offset relative to the penetration member 38. This arrangement is of particular advantage if a preliminary test force is utilized in the process of testing specimens whereby, if a furrow as indicated by the numeral 334 is produced by the penetration member 38, the sensor member 40 will not follow this furrow but rather will move alongside it and is therefore not influenced by the presence of the furrow 334.

Figure 9:
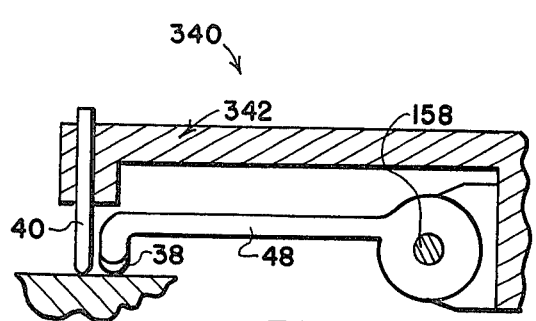
FIG. 9 is a view similar to FIG. 7 of still another alternate embodiment.

Referring to FIG. 9, still another embodiment for mounting penetration and sensor members is indicated generally by the numeral 340. In the embodiment 340, the penetration member is pivotally supported in an arm 48 and a sensor member is slidably supported in a rigid framework 342.

Figure 10:
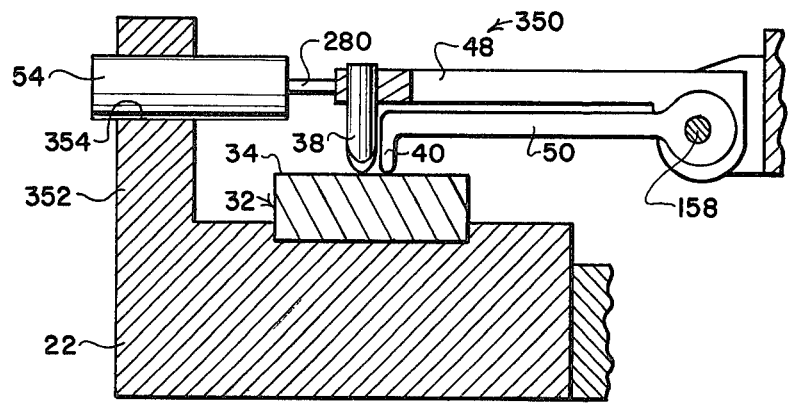
FIG. 10 is a view similar to FIG. 1 of still another embodiment.
Figure 11:
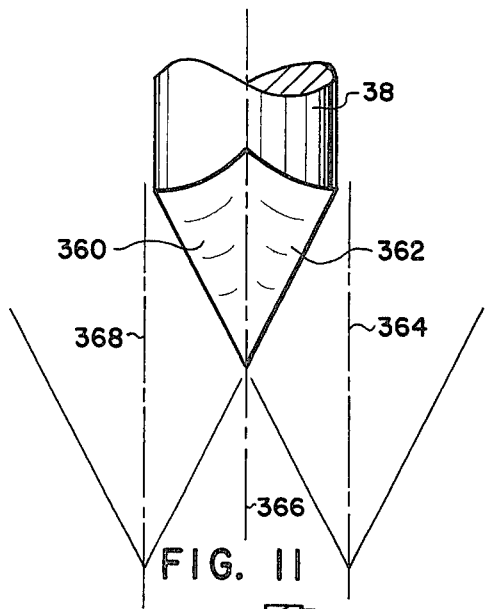
FIG. 11 is an enlarged front elevational view of a penetration point employed on a penetration member utilized in the embodiments of FIGS. 1–10.

Referring to FIG. 10, an alternate location for the transducer 54 is shown in an embodiment 350. In the embodiment 350, the only change which is made over the arrangement shown in FIG. 1 is that the forward base member 22 is provided with an upwardly extending portion 352, a hole 354 is formed in the extended formation 352, and the transducer 354 is supported in the hole 354. The transducer feeler 280 extends into engagement with the penetration member support arm 48 thus eliminating any possible effects of clearance or play, for example such play as may occur in the bearing journaling shaft 158.

Referring to FIG. 10, the preferred type of penetration point used on the penetration member 38 is bounded by two conical surface portions 360, 362. The conical surface portion 360 is formed as part of a cone having an axis 364 which parallels the axis 366 of the penetration member 38 and is spaced to one side thereof. The conical surface portion 362 is formed as part of a cone having an axis 368 which parallels the axis 366 and is spaced symmetrically about the axis 366 from the axis 364. This type of penetration point configuration is relatively easily machined and operates to assure accuracy of the apparatus 20.

Figure 12:
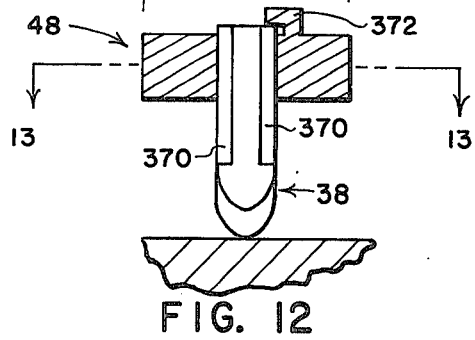
FIG. 12 is a sectional view through a mount in which a penetration member is inserted; and, FIG. 13 is a sectional view as seen from a plane indicated by a line 13—13 in FIG. 12.
Figure 13:
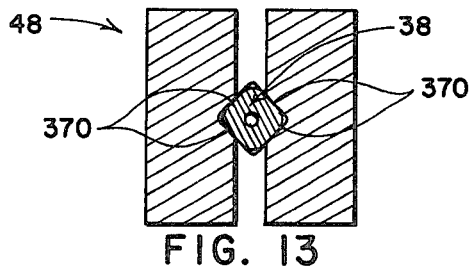

Referring to FIGS. 12 and 13, a preferred mounting arrangement for the penetration member 38 includes the formation of four lateral guide surfaces 370 on the penetration member 38 at a location above its penetration point. Such portions of the penetration member support arm 48 as clamp the penetration member 38 are provided with corresponding surfaces which receive and securely nest the guide surfaces 370. A top abutment member 372 is provided to engage the upper surface of the penetration member 38 to assure its proper positioning relative to the clamping members of the penetration member support arm 48.

Although the invention has been described in its preferred form with a certain degree of particularity, it is understood that the present disclosure of the preferred form has been made only by way of example and numerous changes in the details of construction and the combination and arrangement of parts may be resorted to without departing from the spirit and scope of the invention as hereinafter claimed. It is intended that the patent shall cover, by suitable expression in the appended claims, whatever features of patentable novelty exist in the invention disclosed.

What is claimed is:

1. A surface hardness testing apparatus, comprising:
   a. structure defining a test station adapted to receive and support a test member having a surface which is to be tested for hardness;
   b. penetration member means for contacting and penetrating selected portions of the test surface;

c. sensor member means for gently engaging certain portions of the test surface at a location close beside the penetration member means;

d. penetration member support means for movably mounting the penetration member means for movement toward and away from the plane of the test surface;

e. sensor member support means for movably mounting the sensor member means for movement toward and away from the plane of the test surface;

f. force transmission means for applying a controlled loading to the penetration member means to effect its penetration of the test surface;

g. the penetration member support means and the sensor member support means being operable to permit concurrent lateral movement of the penetration member means and the support member means relative to the test member in directions paralleling the plane of the test surface while maintaining the penetration member means and the sensor member means in closely spaced relationship and without permitting the position and operation of the sensor member means to be influenced by the operation of the force transmission means; and, h. transducer means for sensing relative positioning of the penetration member means and the sensor member means and for providing a corresponding representative output signal.

2. The apparatus of claim 1 wherein the penetration member support means comprises a first arm structure mounted for pivotal movement about a first axis.

3. The apparatus of claim 2 wherein the sensor member support means comprises a guide structure slidably supporting the sensor member for movement along a path of travel extending substantially perpendicularly to the plane of the test surface.

4. The apparatus of claim 2 wherein the sensor member support means comprises a second arm structure mounted for pivotal movement about a second axis.

5. The apparatus of claim 4 wherein the first and second axes are spaced and extend substantially parallel to each other, and the first and second arm members are supported on separate shafts.

6. The apparatus of claim 4 wherein the first and second axes are coaxial, and the first and second arm structures are supported on a common shaft.

7. The apparatus of claim 2 wherein the first and second arm means are supported on first and second pairs of bearings, respectively, and the bearings of each pair are located symmetrically with respect to a common plane of symmetry.

8. The apparatus of claim 1 wherein the force transmission means includes curved-surface force transmitting means interposed between a weight assembly and the penetration member means at a location above the center of gravity of the penetration member means.

9. The apparatus of claim 8 wherein the curved-surface force transmitting means is a ball bearing.

10. The apparatus of claim 8 wherein the force transmitting means further includes weight-force relieving means for selectively applying and relieving controlled weight applied through the curved-surface force transmitting means to the force transmitting means.

11. The apparatus of claim 1 wherein the force transmission means includes weight-force relieving means for selectively applying and relieving controlled weight forces to the penetration member means.

12. The apparatus of claim 1 wherein the transducer means is interposed between the force penetration member means and the sensor member means.

13. The apparatus of claim 1 wherein the penetration member support means includes an abutment for engaging an end portion of the penetration member means to facilitate its positioning within the penetration member support means.

14. The apparatus of claim 1 wherein the penetration member support means includes clamping means for releasably engaging and retaining the penetration member means, and mating guide surface portions are formed on the penetration member support means and the clamping means for facilitating the positioning of the penetration member means within the clamping means.

15. The apparatus of claim 1 wherein the penetration member means has a penetration point for penetrating the test surface, and the penetrating point is defined by two conical surface segments, each of which segments form part of a separate cone, each of which cones have axes which parallel each other and which are located on opposite sides of the penetration member at substantially equal distances therefrom.

* * * * *